(12) United States Patent
Srinivasan

(10) Patent No.: US 9,044,594 B2
(45) Date of Patent: Jun. 2, 2015

(54) LASER GENERATOR FOR DEEP TISSUE LASER TREATMENTS USING LOW INTENSITY LASER THERAPY CAUSING SELECTIVE DESTRUCTION OF NOCICEPTIVE NERVES

(75) Inventor: Pattanam Srinivasan, Lebanon, IN (US)

(73) Assignee: C Laser, Inc., Lebanon, IN (US)

( * ) Notice: Subject to any disclaimer, the term of this patent is extended or adjusted under 35 U.S.C. 154(b) by 0 days.

(21) Appl. No.: 13/329,596

(22) Filed: Dec. 19, 2011

(65) Prior Publication Data

US 2012/0089135 A1    Apr. 12, 2012

Related U.S. Application Data

(63) Continuation-in-part of application No. 13/022,178, filed on Feb. 7, 2011, which is a continuation-in-part of application No. 12/631,835, filed on Jan. 8, 2010.

(51) Int. Cl.
| | |
|---|---|
| A61N 5/067 | (2006.01) |
| A61N 5/06 | (2006.01) |
| A61B 18/20 | (2006.01) |
| A61B 18/00 | (2006.01) |

(52) U.S. Cl.
CPC ....... *A61N 5/0601* (2013.01); *A61N 2005/0626* (2013.01); *A61B 2018/2005* (2013.01); *A61N 2005/0612* (2013.01); *A61N 2005/0662* (2013.01); *A61B 2018/00708* (2013.01)

(58) Field of Classification Search
CPC .............. A61N 2005/0644; A61N 2005/0659; A61N 2005/067; A61N 5/0616
USPC ....................................... 606/2–19
See application file for complete search history.

(56) References Cited

U.S. PATENT DOCUMENTS

| | | | |
|---|---|---|---|
| 4,566,438 A | 1/1986 | Liese et al. | |
| 4,959,063 A | 9/1990 | Kojima | |
| 5,464,436 A | 11/1995 | Smith | |
| 5,772,597 A | 6/1998 | Goldberger et al. | |
| 5,807,261 A | 9/1998 | Benaron et al. | |
| 6,080,148 A | 6/2000 | Damasco et al. | |
| 6,267,779 B1 * | 7/2001 | Gerdes ........................... 607/89 |

(Continued)

FOREIGN PATENT DOCUMENTS

| | | |
|---|---|---|
| DE | 44 29 192 | 2/1996 |
| DE | 200 03 349 | 6/2000 |

(Continued)

OTHER PUBLICATIONS

Morgan & Mikhail, Clinical Anesthesiology, second edition, Chapter 18, Pain Management, pp. 274-280 (12 total pages).

(Continued)

*Primary Examiner* — Aaron Roane

(74) *Attorney, Agent, or Firm* — Fish & Richardson P.C.

(57) ABSTRACT

A laser generator for laser therapy in the treatment of pain conditions by selective destruction of nociceptive or pain nerves, wherein a laser generator that generates a continuous and pulsed laser wavelength between 690 nm to 980 nm that is transmitted fiberoptically through a laser fiber within a spinal needle to contact areas within a body where pain nerves require destruction through optimal absorption of laser energy by pain nerves without affecting other types of nerves or surrounding tissues.

17 Claims, 2 Drawing Sheets

(56) References Cited

U.S. PATENT DOCUMENTS

| | | | |
|---|---|---|---|
| 6,663,659 | B2 | 12/2003 | McDaniel |
| 2003/0120267 | A1 | 6/2003 | Kaufman et al. |
| 2003/0225331 | A1 | 12/2003 | Diederich et al. |
| 2005/0049582 | A1 | 3/2005 | DeBenedictis et al. |
| 2005/0065577 | A1 | 3/2005 | McArthur et al. |
| 2005/0182293 | A1 | 8/2005 | Katzman |
| 2007/0179485 | A1 | 8/2007 | Yeik et al. |
| 2008/0077198 | A1 | 3/2008 | Webb et al. |
| 2008/0125836 | A1 | 5/2008 | Streeter |
| 2009/0069673 | A1 | 3/2009 | Tapalian et al. |
| 2009/0125036 | A1 | 5/2009 | Bleich |
| 2009/0299349 | A1 | 12/2009 | Kubota et al. |
| 2011/0218524 | A1 | 9/2011 | Cattaneo |
| 2011/0301581 | A1 | 12/2011 | Thyzel |

FOREIGN PATENT DOCUMENTS

| | | |
|---|---|---|
| JP | 2009207605 A | 9/2009 |
| KR | 100 963 395 | 6/2010 |
| WO | WO0057804 A1 | 10/2000 |
| WO | WO 01/62171 | 8/2001 |

OTHER PUBLICATIONS http://en.wikipedia.org/wiki/Local anesthetic.
U.S. Non-Final Office Action for U.S. Appl. No. 12/631,835 dated Mar. 14, 2014, 30 pages.
European Office Action in Application No. 11858106.5, dated Sep. 2, 2014, 5 pages.
European Search Report in Application No. 11858106.5, dated Aug. 21, 2014, 3 pages.
Turgut et al.; Extensive Damage to the End-Plates as a Complication of Laser Discectomy An Experimental Study Using an Animal Model; Acta Neurochirurgical 1997; 139: 404-410.
PCT Notification of Transmittal of the International Search Report and the Written Opinion of the International Searching Authority, or the Declaration issued in PCT/US2011/064376 on Feb. 6, 2012, 7 pages.
PCT Notification of Transmittal of the International Search Report and the Written Opinion of the International Searching Authority, or the Declaration issued in PCT/US2011/066006 on Apr. 19, 2012, 7 pages.
U.S. Non-Final Office Action for U.S. Appl. No. 13/022,178 dated Jan. 30, 2014, 18 pages.
U.S. Final Office Action for U.S. Appl. No. 13/022,178 dated Jul. 17, 2014, 15 pages.
PCT International Preliminary Report on Patentability for Application No. PCT/US2011/064376 dated Aug. 13, 2013, 7 pages.
PCT International Preliminary Report on Patentability for Application No. PCT/US2011/066006 dated Aug. 13, 2013, 7 pages.
U.S. Non-Final Office Action for U.S. Appl. No. 12/631,835 dated Dec. 20, 2011, 12 pages.
U.S. Final Office Action for U.S. Appl. No. 12/631,835 dated Mar. 14, 2013, 31 pages.
Tsai et al.; Plasma-mediated ablation: an optical tool for submicrometer surgery on neuronal and vascular systems; Science Direct, Current Opinion in Biotechnology 2009, 20:1-10; www.sciencedirect.com.
Singh et al.; Percutaneous Lumbar Laser Disc Decompression: A Systematic Review of Current Evidence; Pain Physician 2009; 12:573-588 ISSN 1533-3159; www.painphysicianjournal.com.
Schenk et al.; Percutaneous Laser Disk Decompression: A Review of Literature; AJNR 27; Jan. 2006; www.ajnr.org.
U.S. Non-Final Office Action for U.S. Appl. No. 12/631,835 dated Sep. 4, 2012, 25 pages.
U.S. Final Office Action for U.S. Appl. No. 12/631,835 dated Jun. 19, 2012, 19 pages.
U.S. Non-Final Office Action for U.S. Appl. No. 13/022,178 dated Dec. 20, 2011, 11 pages.
U.S. Final Office Action for U.S. Appl. No. 13/022,178 dated Feb. 13, 2013, 14 pages.
U.S. Non-Final Office Action for U.S. Appl. No. 13/022,178 dated Aug. 17, 2012, 13 pages.
European Search Report issued in Application No. 11858224.6 on Feb. 27, 2015, 3 pages.
Communication Pursuant to Article 94(3) EPC issued in EP 11858224.6 on Mar. 19, 2015, 5 pages.

* cited by examiner

LASER GENERATOR FOR DEEP TISSUE LASER TREATMENTS USING LOW INTENSITY LASER THERAPY CAUSING SELECTIVE DESTRUCTION OF NOCICEPTIVE NERVES

CROSS REFERENCES TO RELATED APPLICATIONS

This application is a Continuation-in-Part of U.S. patent application Ser. No. 13/022,178, filed Feb. 7, 2011, which is a Continuation-In-Part of U.S. patent application Ser. No. 12/631,835, filed Feb. 21, 2010, the entirety of each of which are herein incorporated by reference.

BACKGROUND OF THE INVENTION

The present invention relates to laser generating medical devices that deliver laser energy to nerve endings deep within the body to alleviate pain in a technique known to the present inventor as deep tissue low intensity laser neuroablation, as more fully described in the related applications incorporated herein by reference.

BRIEF SUMMARY OF THE INVENTION

The present invention is a laser generator for deep tissue laser treatments using low intensity laser therapy that causes selective destruction of nociceptive nerves deep within the body.

One embodiment of the present invention is a laser generator for laser therapy in the treatment of pain conditions by selective destruction of nociceptive or pain nerves, comprising a laser generator that generates a continuous and pulsed laser wavelength between 690 nm to 980 nm that is transmitted fiberoptically through a laser fiber within a spinal needle to contact areas within a body where pain nerves require destruction through optimal absorption of laser energy by pain nerves without affecting other types of nerves or surrounding tissues.

BRIEF DESCRIPTION OF THE DRAWINGS

The figures are for illustration purposes only and are not necessarily drawn to scale. The invention itself, however, may best be understood by reference to the detailed description which follows when taken in conjunction with the accompanying drawings in which.

DETAILED DESCRIPTION OF THE INVENTION

Definition of Terms

Figure 1:
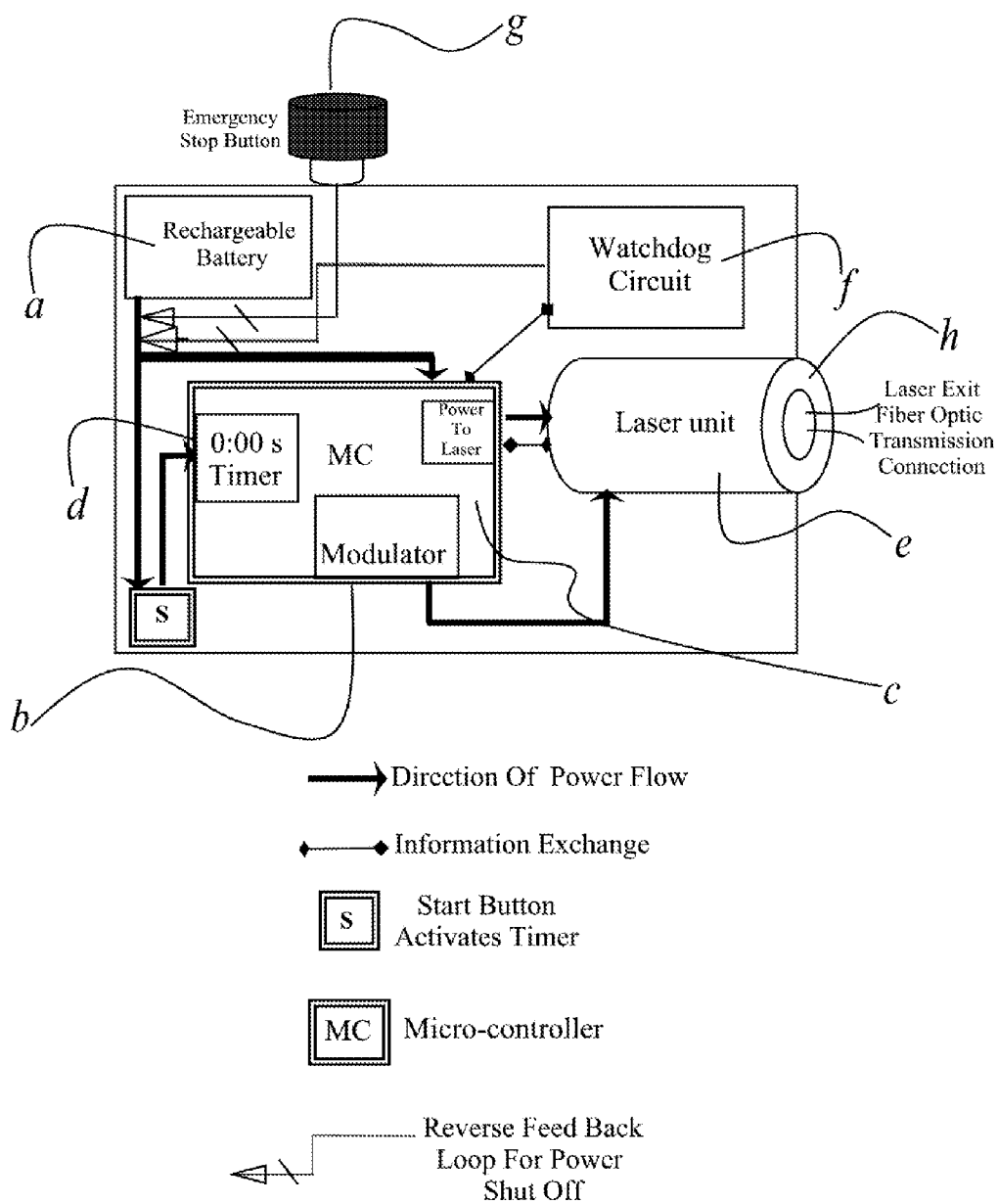
FIG. 1 is a schematic diagram of the laser generator of the present invention.

1. LILA: Low Intensity Laser Ablation
2. DT-LILT: Deep Tissue Low Intensity Laser Treatment or Therapy.
3. DT-LIL: Deep Tissue Low Intensity Laser.
4. DT-LILA: Deep Tissue Low Intensity Laser Ablation.
5. DT-LILNA: Deep Tissue Low Intensity Laser Neuroablation.

The use of terms DT-LILT, DT-LIL and DT-LILA was first described in co-pending U.S. patent application Ser. No. 12/631,835 entitled "Method for Deep Tissue Laser Treatments Using Low Intensity Laser Therapy Causing Selective Destruction of Nociceptive Nerves." LILA or Low Intensity Laser Ablation as used herein is used as a general term identifying ablation or destruction of tissues using a low intensity laser.

The low intensity laser generator of the present invention is capable of producing cell resonance within nerve cells that can selectively cause destruction of the nerve cells without affecting the surrounding tissues. The selection of the laser wavelength will depend on the absorption characteristics of the targeted nerve cells. Heat may or may not be generated, but is not needed as the selective destruction of the targeted nerve cells takes place by cell resonance rather than by heat coagulation.

The use of the laser generator of the present invention is different from the use previously made of other medical or tissue lasers whose primary effect has been through heat generation. The physical phenomena of such laser effects have been described in laboratory experiments. CARS (Coherent Anti-Stokes Raman Spectroscopy) microscopy is one field where lasers have been used to observe live tissues, including nerve cells. Nerve cells are optimally observed at the NIR (near infra-red) wavelengths especially at the 700-705 nm range. Such observation using lasers has to be concluded within a few seconds, and in most instances in less than a second, as the nerve cells are readily destroyed by the laser. Within this short time, it appears that the absorbed laser energy has nowhere to go, resulting in cellular plasma expansion and cell disruption. During plasma expansion there is vibration or resonance that leads to cell breakage. It is not necessary to determine the cell resonance, as it spontaneously occurs on absorption of laser energy specific to the nerve cells. This is an unwanted effect during microscopic observations of live nerve cells. Other experiments have documented that round worm nerve cells have been destroyed by NIR wavelengths using ultrafast lasers. None of the apparatus used in microscopy observations, or that used to destroy round worm nerve cells, are usable within humans, and the physical phenomena of laser effects described thus far have had no clinical use except as described by the present inventor in co-pending U.S. patent application Ser. No. 12/631,835, entitled "Method for Deep Tissue Laser Treatments Using Low Intensity Laser Therapy Causing Selective Destruction of Nociceptive Nerves."

Furthermore Deep Tissue Low Intensity Laser Therapy (DT-LILT) as described herein enables the therapeutic use of lasers by putting them in direct and precise contact with the area of treatment even though such treatment areas may lie quite deep within the human body. The present inventor through his unpublished clinical observations using the laser generator of the present invention has determined that small pain nerves are readily destroyed within 5 seconds of laser contact at the area of treatment. The nerve cell destruction takes place within a fraction of a second, therefore for practical purposes a 5 second exposure appears to be supra maximal or more than optimal. The small pain nerves also known as C pain fibers do not have myelin sheaths, the outer covering present in other types of nerves. Lack of this myelin sheath or having a thin insignificant outer membrane makes these nerves susceptible to low power laser energy.

Nerve cell composition plays a significant role in laser wavelength absorption. For example, flavins, a type of proteins present in nerve cells, may make these susceptible to laser wavelengths of 440 nm to 460 nm, while the increased fat or lipid content present in nerve cells may make them susceptible to laser treatment at the 690-710 nm wavelength, as well as those close to 980 nm in the infra-red region. The 980 nm laser wavelength is widely used for liposuction laser surgery but not for pain relief.

The laser generator of the present invention is capable of generating the appropriate wavelengths, which are desirably in the 690 nm to 710 nm range. No other contact medical or tissue laser devices exist in the world today that generate wavelengths between the 690 nm to 710 nm range except those described in the present application.

The ideal laser generator characteristics of the present invention are:

1. Laser Wavelengths of 700 nm to 705 nm. Other wavelengths that are capable of absorption by nerve cells include those in the blue spectrum of 450 to 460 nm and those above 900 nm, for example, 980 nm. The 980 nm wavelength is preferentially absorbed by lipids that are abundant in the nerve cells.
2. Laser Output Average Power: 4 mW to 6 mW (range 1 mW to 6 mW).
3. Laser Pulsation: pulse width of nano seconds or picoseconds matched with appropriate frequency in megahertz (MHz) or higher.
4. Laser is Timer controlled: 5 s and 10 s.

The laser generator of the present invention is illustrated schematically in FIG. 1 where the internal components are described. These internal components form the laser generator of the present invention for generating the low intensity laser for deep tissue low intensity laser neuroablation. Essential components include a power source (a), which in this case is a rechargeable battery whose power output will power the laser generator. The laser generator contains an electronic modulator (b) that enables generation of high speed pulsation in nano seconds or faster. The modulator can generate non-pulsed continuous signals, as well. The choice of using a pulsed signal or non-pulsed signal is controlled by a microcontroller (c) through user input. An electronic timer controller (d) is added within the circuit that is activated during the operation of the laser unit for time limiting the laser delivery. The laser generator has a laser unit (e) that incorporates a laser diode generating the required wavelength of 700-705 nm. Such laser diodes are commercially available (see, e.g., Opnext HL 7001). The laser unit incorporates a driver and an electronic circuit to receive power input and pulse signals from the modulator, and on activation is able to output a laser of low power between 1 mW to 6 mW, which can also have simultaneous pulsation with pulse width in nano seconds or shorter. The timer, modulator and the power input to the laser unit are all embedded within a micro-controller (c). The power input to the laser unit is also regulated by the micro-controller.

The laser generator is organized to provide non-pulsed continuous waves through use of the same modulator. However using pulsation helps prevent heat generation by further reducing the average power output. Although laser units with various wavelengths are available from different manufacturers (see, e.g., PowerTech), but the present laser generator invention is the first such laser unit that may be incorporated in an apparatus to generate the intended low intensity medical laser output for pain relief.

An additional element in the laser generator of the present invention is the inclusion of a watchdog circuit (f). The watchdog circuit monitors the health of the electronic apparatus and interrupts the laser delivery when operating parameters exceed a certain level, and hence performs an important safety role required of medical devices. In this case, the watchdog circuit is activated when the timer controller fails and the laser delivery time exceeds the set limit. When the watchdog circuit is activated, power source to the laser unit will be interrupted, terminating the laser output with immediate effect. A user operated emergency shut off button (g) also forms a part of the laser generator, a component required of medical devices of this kind. When pressed by the physician or equivalent user, the power source to the apparatus is interrupted, resulting in immediate shutdown of the apparatus.

The laser generator also has an optical fiber attachment port, also called the fiber port, (h) that is the starting point of the fiber optic transmission. The proximal end of a fiber optic delivery system would attach to this fiber port. This fiber port may receive standard fiber attachments (e.g., SMA 905 type) or custom nonstandard size to prevent cross connections of fibers of other medical or non-medical devices. With the help of such an attachment, the low intensity laser generated is able to be delivered distally in the human body.

In unpublished experiments to date initiated by the present inventor, the laser generator of the present invention appears to provide neuroablative affect in animals. The present inventor has also determined through unpublished Institutional Review Board (IRB) approved clinical trials to date that pain relief is obtained in humans with the use of the laser generator of the present invention.

Figure 2A:
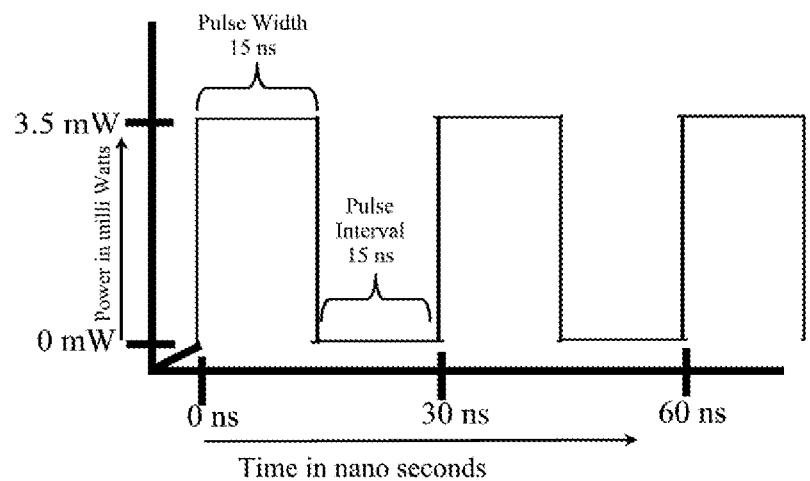
FIG. 2a is a graphical representation of pulse wave generated by a laser generator of the present invention when the pulse width is 15 nano seconds.
Figure 2B:
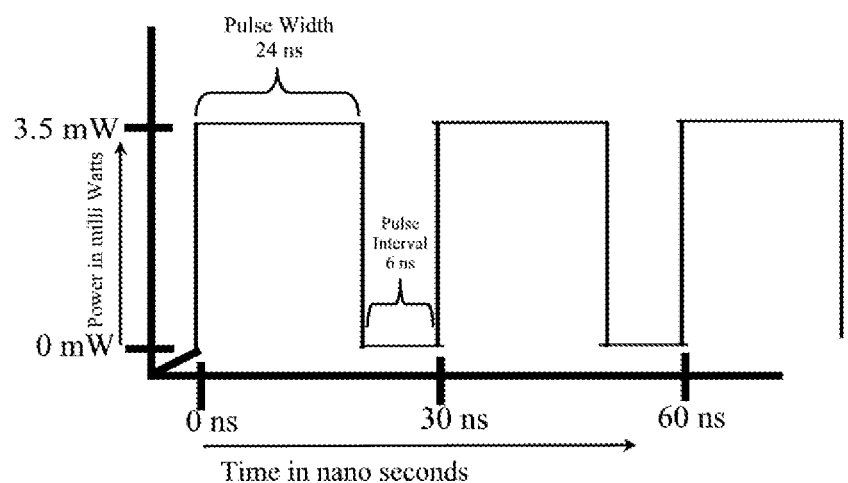
FIG. 2b is a graphical representation of pulse wave generated by a laser generator of the present invention when the pulse width is 24 nano seconds.

An apparatus consisting of the laser generator of the present invention and a delivery system that is able to deliver a pulsed 705 nm laser to the tip of a needle has a laser output power ranging from 3 mW to 4.5 mW. At 24 nano second pulse width and 33 Mega Hertz (MHz) high frequency pulsation, the laser generator delivers an average power of 1.75 mW at the needle tip with a peak power of 3.5 mW. The corresponding pulse wave generated at this setting is shown schematically (not to scale) in FIG. 2a. At 24 nano second pulse width and 33 Mega Hertz (MHz) high frequency pulsation, the laser generator delivers an average power of 2.8 mW at a needle tip with a peak power of 3.5 mW. The corresponding pulse wave generated at this setting is shown schematically (not to scale) in FIG. 2b. From FIGS. 2a and 2b, it is obvious that while the peak power remains at 3.5 mW, the average power is reduced to 2.8 mW because of the pulse interval when no energy is delivered.

The laser generator of the present invention has the ability to provide immediate pain relief through selective neuroablation of nociceptive or pain fibers by using either continuous wave or pulsed wave.

The laser generator of the present invention also has several non-specific enhancements created that are common to electronic or medical devices in use today. These include a user (physician or an equivalent professional) interactive touch screen that controls the apparatus through software and hardware operations, and a foot pedal for timer controlled laser activation that is very convenient to use.

I claim:
1. A laser generator for laser therapy in treatment of pain conditions by selective destruction of nociceptive or pain nerves, comprising;
an electronic modulator that is configured to generate one of a continuous non-pulsed signal or a pulsed signal including a wavelength in a specified range;
a laser unit that is configured to generate a laser, wherein the laser unit is coupled to the electronic modulator such that the laser generator outputs a laser signal that is one of a continuous non-pulsed laser signal or a pulsed laser signal, wherein the laser signal includes a wavelength in the specified range;

an electronic timer controller that is configured to be activated during operation of the laser unit and operable to limit delivery time of the laser; and a watchdog circuit that is configured to perform operations including:

monitoring the delivery time of the laser;

comparing the delivery time of the laser to a predetermined threshold;

in response to the comparing, determining whether the delivery time of the laser exceeds the predetermined threshold;

based on determining that the delivery time of the laser exceeds the predetermined threshold, determining that the electronic timer controller has failed; and in response to determining that the electronic timer controller has failed, terminating the laser signal that is output by the laser generator by interrupting power source to the laser unit.

2. The laser generator of claim 1, wherein the laser signal includes a wavelength that is between 700 nm to 705 nm.

3. The laser generator of claim 1 wherein the laser wavelength is between 440 to 460 nm.

4. The laser generator of claim 1, wherein the electronic modulator is configured to generate the pulsed signal including a pulse width in a range of nanoseconds, and wherein the laser generator is operable to output the pulsed laser signal including a 33 MHz high frequency pulsation and a pulse width that is one of 15 nanoseconds or 24 nanoseconds.

5. The laser generator of claim 4, including a power source that is configured to output power within a range between 1 mW to 6 mW, whereby heat generation is prevented through low energy laser outputs, preserving integrity of nonpain nerves and surrounding tissues.

6. The laser generator of claim 5, wherein the laser generator is operable to output an average power in a range of 1.75 mW with a peak power in a range of 3.5 mW associated with the pulsed laser signal that includes the 33 MHz high frequency pulsation and the pulse width of 15 nanoseconds.

7. The laser generator of claim 5, wherein the laser generator is operable to output an average power in a range of 2.8 mW with a peak power in a range of 3.5 mW associated with the pulsed laser signal that includes the 33 MHz high frequency pulsation and the pulse width of 24 nanoseconds.

8. The laser generator of claim 5, wherein the power source includes a rechargeable battery.

9. The laser generator of claim 1, comprising a user interface, wherein operation of the laser generator is controllable via user inputs provided through the user interface.

10. The laser generator of claim 9, wherein the user interface includes a touchscreen user interface.

11. The laser generator of claim 1 and further comprising a user operated shutoff button for emergency shutdown.

12. The laser generator of claim 1, comprising a microcontroller, wherein the electronic modulator and the electronic timer are included in the microcontroller.

13. The laser generator of claim 12, wherein the microcontroller includes a power unit that is configured to control an amount of power that is provided to the laser unit.

14. The laser generator of claim 13, wherein the laser unit includes a includes a first input that is configured to receive power from the power unit, and a second input that is configured to receive one of the continuous non-pulsed signal or the pulsed signal from the electronic modulator, and wherein the laser unit is operable to output the laser signal with power in a range between 1 mW to 6 mW.

15. The laser generator of claim 1, wherein the electronic timer controller is operable to limit the delivery time of the laser to one of 5 seconds or 10 seconds.

16. The laser generator of claim 1, comprising a fiber port that is configured to:

couple a fiber optic delivery system to the laser generator; and transmit the laser signal that is output by the laser generator to the fiber optic delivery system for delivery to a treatment area.

17. The laser generator of claim 1, wherein the specified range of the wavelength is between 690 nm and 980 nm.

\* \* \* \* \*

UNITED STATES PATENT AND TRADEMARK OFFICE
CERTIFICATE OF CORRECTION

| | | |
|---|---|---|
| PATENT NO. | : 9,044,594 B2 | Page 1 of 1 |
| APPLICATION NO. | : 13/329596 | |
| DATED | : June 2, 2015 | |
| INVENTOR(S) | : Pattanam Srinivasan | |

It is certified that error appears in the above-identified patent and that said Letters Patent is hereby corrected as shown below:

In the claims

Column 6, line 22, Claim 14, please delete "includes a includes a" and insert therefor -- includes a --.

Signed and Sealed this
First Day of December, 2015

Michelle K. Lee
*Director of the United States Patent and Trademark Office*